(12) United States Patent
Parsonage et al.

(10) Patent No.: US 6,841,213 B2
(45) Date of Patent: Jan. 11, 2005

(54) FIBER PATTERN PRINTING

(75) Inventors: Edward Parsonage, St. Paul, MN (US); Paul J. Miller, St. Paul, MN (US)

(73) Assignee: SciMed Life Systems, INC, Maple Grove, MN (US)

( * ) Notice: Subject to any disclaimer, the term of this patent is extended or adjusted under 35 U.S.C. 154(b) by 0 days.

(21) Appl. No.: 10/330,506

(22) Filed: Dec. 27, 2002

(65) Prior Publication Data

US 2004/0126526 A1 Jul. 1, 2004

(51) Int. Cl.$^7$ ............................................. A61M 25/16
(52) U.S. Cl. .................... 428/35.7; 427/2.24; 427/181; 427/183; 427/197; 427/200; 428/36.3; 428/36.9; 428/36.91
(58) Field of Search ................. 427/2.24, 181, 427/183, 197, 200; 428/35.7, 36.3, 36.9, 36.91

(56) References Cited

U.S. PATENT DOCUMENTS

| | | | |
|---|---|---|---|
| 4,732,152 A | 3/1988 | Wallsten et al. ............ 623/1.11 |
| 4,793,348 A | 12/1988 | Palmaz ...................... 606/194 |
| 4,848,343 A | 7/1989 | Wallsten et al. ............ 606/194 |
| 4,875,480 A | 10/1989 | Imbert ........................ 606/194 |
| 4,950,227 A | 8/1990 | Sarin et al. ................. 623/1.12 |
| 5,108,416 A | 4/1992 | Ryan et al. .................. 606/194 |
| 5,403,341 A | 4/1995 | Solar .......................... 606/198 |
| 5,662,703 A | 9/1997 | Yurek et al. ................. 623/1.12 |
| 5,690,644 A | 11/1997 | Yurek et al. ................ 623/1.12 |
| 5,746,745 A | 5/1998 | Abele et al. ................ 623/1.11 |
| 5,772,669 A | 6/1998 | Vrba .......................... 623/1.11 |
| 5,868,755 A | 2/1999 | Kanner et al. .............. 606/108 |
| 5,888,577 A * | 3/1999 | Griffin et al. ................. 427/2.3 |
| 6,048,350 A | 4/2000 | Vrba .......................... 623/1.11 |
| 6,146,814 A * | 11/2000 | Millet ......................... 430/320 |
| 6,183,505 B1 | 2/2001 | Mohn, Jr. et al. .......... 623/1.11 |
| 6,258,099 B1 | 7/2001 | Mareiro et al. ............. 606/108 |
| 6,306,144 B1 | 10/2001 | Sydney et al. .............. 606/108 |
| 6,447,835 B1 | 9/2002 | Wang et al. ................ 427/2.24 |
| 6,458,138 B1 | 10/2002 | Sydney et al. .............. 606/108 |
| 6,494,894 B2 | 12/2002 | Mirarchi ..................... 606/190 |
| 6,616,765 B1 * | 9/2003 | Castro et al. ............... 118/669 |
| 6,656,211 B1 * | 12/2003 | DiCaprio .................... 623/1.11 |

FOREIGN PATENT DOCUMENTS

| EP | 0 696 447 B1 | 1/2000 |
| WO | 94/15549 A1 | 7/1994 |
| WO | 00/57816 A1 | 10/2000 |

OTHER PUBLICATIONS

U.S. patent application Ser. No. 09/697,608, DiCaprio, filed Oct. 26, 2000.

* cited by examiner

*Primary Examiner*—Sandra M. Nolan
(74) *Attorney, Agent, or Firm*—Vidas, Arrett & Steinkraus, P.A.

(57) ABSTRACT

A substantially tubular member comprises a body. The body is constructed from a first material and has an external surface. At least a portion of the external surface has a predetermined pattern of a second material deposited thereon. The predetermined pattern of the second material is deposited on the at least a portion of the external surface by one or more printing processes such as solution coating, spray coating, thermal printing, piezo jet printing, contact printing and any combination thereof.

26 Claims, 6 Drawing Sheets

FIBER PATTERN PRINTING

CROSS-REFERENCE TO RELATED APPLICATIONS

Not Applicable

STATEMENT REGARDING FEDERALLY SPONSORED RESEARCH

Not Applicable

BACKGROUND OF THE INVENTION

The use of catheters and medical balloons therewith, for delivery of an expandable, implantable medical device such as a stent, stent-graft, graft or vena cava filter to a desired bodily location are well known in the art. Typically, an expandable, implantable medical device such as a stent is disposed about a balloon which in turn is mounted on a catheter tube. The catheter is inserted into a bodily vessel and advanced to a desired location. The balloon is then inflated so as to expand or assist in expanding the medical device. Where the implantable medical device is self-expandable the catheter may be equipped with a medical device retaining region in addition to or in place of the medical balloon.

The term 'catheter' as used herein is directed to medical devices such as guide catheters, delivery catheters, balloon catheters, and portions thereof, including but not limited to inflatable members such as balloons.

In delivering a balloon expandable medical device, it is important that the medical device be accurately positioned on the body or working portion of the balloon. Failure to properly position the medical device on the balloon may result in a non-uniform expansion of the medical device.

Unfortunately, the proper positioning of such a medical device on a balloon catheter can be a challenging task because the medical device is typically mounted on an uninflated balloon.

Numerous devices have been employed to help secure an expandable medical device, such as a stent onto a catheter. Such devices include pull-back sheathes which extend over the entire stent to retain the stent to a portion of the catheter. Some examples of sheathes may be found in U.S. Pat. No. 5,772,669, U.S. Pat. No. 5,868,755, U.S. Pat. No. 4,732,152, U.S. Pat. No. 4,848,343, U.S. Pat. No. 4,875,480, U.S. Pat. No. 5,662,703, U.S. Pat. No. 5,690,644, WO 94/15549 and others. With many retraction systems, it is necessary to move a portion of a manifold or other retraction device a distance at least equal to the length of the retractable sheath to retract the sheath.

Some systems have been developed which avoid the need for retractable sheathes by providing a stent delivery catheter with one or more self-retracting sleeves. Some examples of delivery catheters having sleeves which may be self-retractable are described in: U.S. Pat. No. 4,950,227, U.S. Pat. No. 5,403,341, U.S. Pat. No. 5,108,416, and others.

In U.S. Pat. No. 4,950,227 to Savin et al., an inflation expandable stent delivery system includes a sleeve which overlaps the distal or proximal margin (or both) of the stent during delivery. During inflation of the stent at the deployment site, the stent margins are freed of the protective sleeve(s). U.S. Pat. No. 5,403,341 to Solar, relates to a stent delivery and deployment assembly which uses retaining sheaths positioned about opposite ends of the compressed stent. The retaining sheaths of Solar are adapted to tear under pressure as the stent is radially expanded, thus releasing the stent from engagement with the sheaths. U.S. Pat. No. 5,108,416 to Ryan et al., describes a stent introducer system which uses one or two flexible end caps and an annular socket surrounding the balloon to position the stent during introduction to the deployment site.

Still other systems are known which employ a variety of alternative means for retaining a stent on a catheter prior to deliver. For example, the stent delivery system of U.S. patent application Ser. No. 09/697,608 includes stent securement hubs which engage portions of a stent disposed about a catheter, and EP 696,447 describes delivery catheters comprising runners for circumferentially supporting a prosthesis.

Still other systems have been developed which employ surface features on the catheter surface to aid in retaining the stent thereabout. Some examples of systems having unique surface features are described in: WO 00/57816 wherein catheters are described having a textured or roughened surface for retaining a medical device thereon, U.S. Pat. No. 6,258,099 which describes catheter balloons having engagement protrusions, and U.S. Pat. No. 6,048,350 which describes delivery systems employing a combination of securement hubs and balloon segments to aid in retaining a stent there on.

An advantage of providing a stent delivery catheter and/or balloon with surface features that promote stent retention prior to delivery is that the profile of the catheter may be minimized as there may be no need to include additional sheathes, sleeves or other members which would otherwise overlap the stent and increase the profile of the catheter. Another advantage of providing a catheter with stent retaining surface features is that by removing the need for retractable members, the need for relatively bulky or complex retraction systems is likewise removed, thereby providing a delivery system which may be much more simple and safer to use.

Expandable medical devices such as stents have a wide variety of shapes, sizes and configurations. For example, it is known that a stent having a particular strut pattern may have performance characteristics which are significantly different than a stent having a different strut pattern. As a result, it would be desirable to provide individual catheters with varying types of surface feature patterns in order to maximize the effectiveness of the surface pattern in retaining a stent of a particular configuration. Unfortunately, typical manufacturing processes of catheters do not readily lend themselves to individualized production of different catheter types.

Typically, catheters are formed of extruded material which is then shaped or molded into the final catheter shape. Providing dozens of different molds for a wide range of surface feature patterns may be cost prohibitive as well as extremely inefficient from a manufacturing perspective. Thus, it would be desirable to provide a method for applying a unique surface feature pattern to catheters which may be cheaply and easily employed on an individual basis.

All U.S. patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

The present invention includes many different embodiments. Some of the embodiments are directed to catheters in general and in some embodiments to catheter balloons for angioplasty or advantageously for use in the delivery of medical devices such as stents.

Some embodiments of the invention are directed to catheters having a textured, partially textured or otherwise marked surface which provides the catheter with improved stent retaining characteristics. The texturing or marking facilitates the positioning of an expandable, implantable medical device on the catheter and increases the securement of a stent or other expandable, implantable medical device to the catheter.

In at least one embodiment of the invention, a catheter, balloon or other tubular shaft may be provided with a deposited pattern of material. The deposited material may be characterized as any material that may be used to modify the physical properties of the tubing, such as for example flexibility, via the configuration, location, and/or other characteristic of the pattern and the physical properties of the deposited material.

In at least one embodiment, the material deposited on the catheter or balloon shaft is a fibrous material. In some embodiments the material may be, but is not limited to: thermoplastics, thermoset polymers, inorganic ceramics, metals, etc.

In at least one embodiment, the deposited material is provided with a pattern which is constructed and arranged to improve retention and engagement between the catheter and/or balloon surface and a stent or other implantable medical device that may be disposed thereabout.

In at least some embodiments, the deposited pattern of material is of a material having a different composition than that of the underlying catheter or balloon tubing.

In at least one embodiment of the invention, material deposited on a balloon or catheter is a continuous film. Alternatively the deposited material may be a discontinuous coating or deposit. The deposited material may be deposited on the tubing in a pattern comprised of features such as helical, longitudinal, crossed, and/or radial stripes, or any pattern desired. In some embodiments of the invention, the deposited material is oriented on the tubing in one or more longitudinally tapering stripes.

In some embodiments where the invention is directed to a balloon, the surface of the balloon is provided with one or more deposited struts of material which act to provide the balloon with uniform inflation characteristics. During balloon inflation, the strut or struts can act to transfer stress from the ends of the balloon to the middle portion of the balloon.

In some embodiments of the invention, material deposited on a catheter or balloon, is deposited by one or more techniques including: solution coating, spray coating, thermal printing, piezo jet printing, contact printing, etc.

In at least one embodiment of the invention, the particular method utilized to deposit the material on the catheter/balloon tube may include one or more of the following steps: a curing step or steps, initial surface treatment step or steps, a post-deposition processing step or steps, etc.

In the various embodiments of the invention, the resulting selectively coated catheter and/or balloon tubular member will be provided with one or more physical characteristics that are different than the tubular member would have had without the deposition of material. Through the application of a deposited material to a tubular member, for use as a catheter, balloon or other medical device, the tubular member may be provided with a variety of desired performance characteristics. Some examples of characteristics that may be altered or improved according to the present invention include but are not limited to: flexular modulus, elasticity, columnar strength, kink resistance, burst pressure, compliance, among others.

Additional details and/or embodiments of the invention are discussed below.

BRIEF DESCRIPTION OF THE SEVERAL VIEWS OF THE DRAWINGS

A detailed description of the invention is hereafter described with specific reference being made to the drawings.

DETAILED DESCRIPTION OF THE INVENTION

Figure 1:
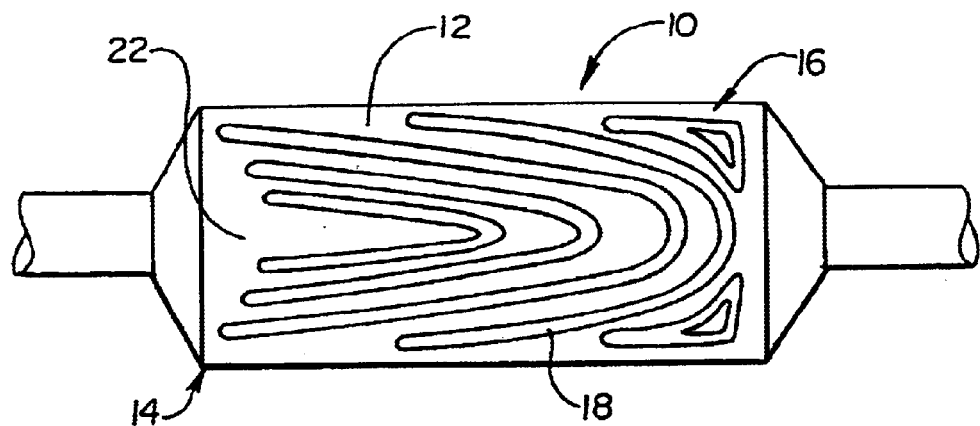
FIG. 1 is a side elevational view of an embodiment of the invention wherein a portion of a catheter is shown with one a pattern of material placed thereon.

The present invention includes many different embodiments. For example, in FIGS. 1 and 2 embodiments of the invention are shown wherein different forms of medical device, such as a catheter 10 are respectively depicted. Catheter 10 may be any type of elongate medical device or portion thereof, such as a balloon, capable of being inserted into a body lumen and advanced therethrough. Numerous types and configurations of such medical devices are known and the term "catheter" as used herein is merely a convenient term used to designate all such devices.

In the various embodiments described herein, catheter 10 may be manufactured from a catheter material or tube 12. The catheter 10 includes a distal region 14 which has an outer surface 16 having a pattern of indented or raised material 18 thereon.

In some embodiments, a deposited material 18 can be characterized as being soft or tacky when compared to the surrounding material 12. However, material 18 that is comparatively hard, relative to the catheter material 12 may also be used. In some embodiments of the invention, the materials 12 and 18 may be the same or have similar characteristics.

Figure 2:
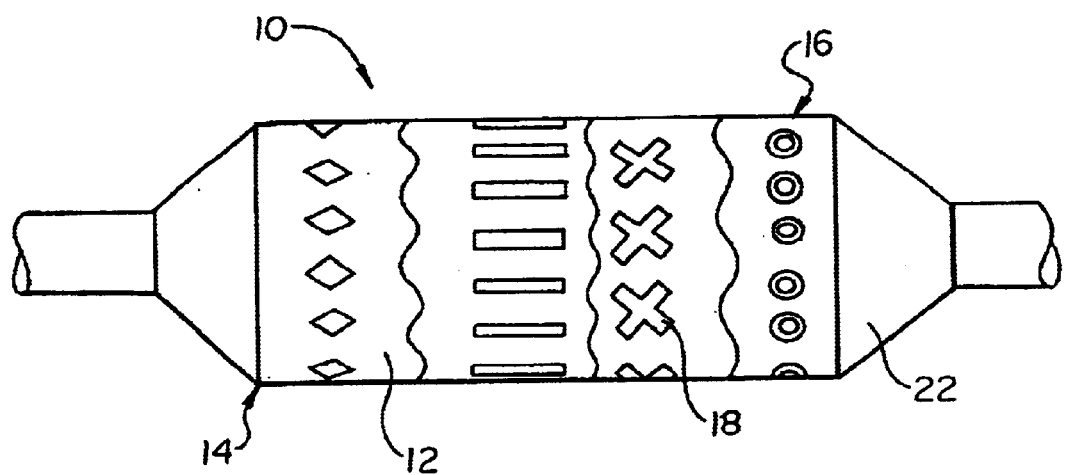
FIG. 2 is a side elevational view of an embodiment of the invention wherein a portion of a catheter is shown with one a pattern of material placed thereon.
Figure 3:
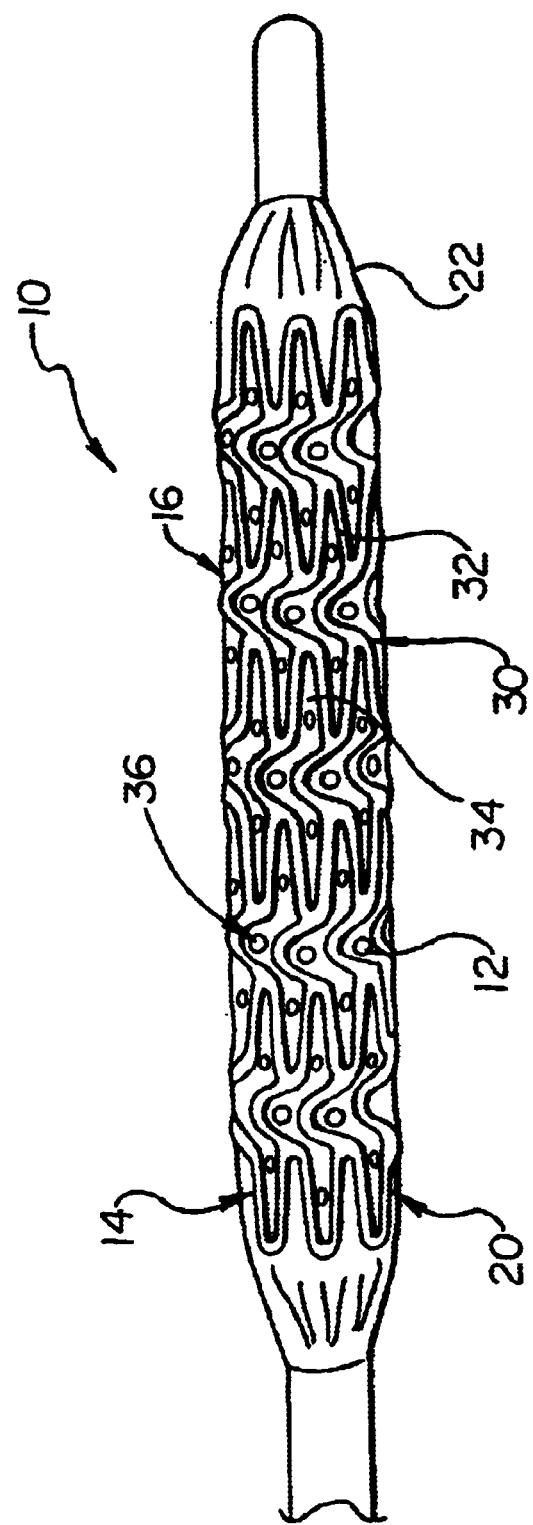
FIG. 3 is a side elevational view of an embodiment of the invention illustrating the engagement of a medical device to a catheter having a pattern of material which corresponds to openings in the framework of the medical device.

FIGS. 1 and 2 illustrate merely two potential patterns of material 18 which a catheter 10 may be configured with. As is shown in FIG. 3, such unique patterns are useful in securing an expandable medical device, such as for example a stent 20 to the catheter surface 16 prior to delivery of the stent 20.

As is known, medical devices such as stents may be self-expandable, balloon expandable or maybe a hybrid of the two more common types. Stents of all types may be included with appropriate embodiments of the present invention. For example, in order to deliver and expand a balloon expandable stent, the distal region 14 of the catheter 10 may be equipped with an expandable member or balloon 22. Where stent 20 is a self-expanding stent or a hybrid device, balloon 22 may be used to trigger or aid in stent delivery and may further be used to seat the stent into place within the body lumen.

In the embodiments shown in FIGS. 1 and 2 the distal region 14 may include a balloon 22 therewith. Where any embodiment of the present invention includes a balloon 22, it is understood that the catheter 10 will further include an inflation means such as an inflation lumen or similar device (not shown) to inflate the balloon 22 for stent delivery or other purposes as is known in the art.

In various embodiments of the invention, the material 18 may be characterized as any substance or substances that alter the physical properties of the catheter 10, such as the ability of the catheter surface 16 to interact with a medical device such as stent 20 disposed thereabout. For example, where the material 18 is a higher modulus material than the catheter material 12, the material 18 may provide the catheter 10 with improved ability to removably engage the stent 20 mounted thereon such as is shown in FIGS. 3 and 6. A wide variety of substances may comprise material 18. Material 18 may include, but is not limited to: thermoplastics, thermosets, inorganic ceramic substances, metals, and/or any other substance desired.

In some embodiments, the material 18 is a fibrous material comprising organic and/or inorganic thermoset compositions. Some organic thermoset compositions may comprise for example: linear or branched resin systems containing epoxy, urethane, imide, ester, ketene, sulphone or urea functionalities. Organic thermosets may also contain vinyl or allylic functionalities, such as vinyl esters and cyanoacrylates, for example. Phenolic and silicone containing resins would also be included. Inorganic fibrous materials may contain thermoset compositions comprising alkoxides of silicon, aluminum, titanium, zirconcium, etc. In some embodiments carbon fiber may also be used.

In addition to organic thermoset polymers, inorganic thermoset polymers and blends thereof, some embodiments of the invention may include a material 18 that is a thermoset composition comprising mesogenic functionalities which provide liquid crystalline properties to the thermoset. For example, in at least one embodiment, material 18 includes resin compositions having planar aromatic functionalities such as: 4-4'-di(2,3 epoxypropyloxy) phenyl benzoate, diamino diphenyl ester, 2,6 napthalene-di[4-(2-propenyloxy) benzoate], diamino diphenly sulfone, methylene dianiline, dicyatonapthalene, resorcinol diglycidyl ether, diaminonapthalene, napthalene diol, and p-phenylene diamine among others.

In some embodiments fibrous material 18 may contain additional fillers to enhance the properties of the thermoset. These fillers may be conventional fillers such as glass fiber, carbon, etc. In some embodiments the material may contain nanocomposite fillers such as intercalated and/or exfoliated clays such as, for example: montmorillonite, hectorites, hydrotalcites, vermiculite, and laponite. Other filler materials include, for example, monomeric silicates such as polyhedral oligomer silesequioxanes (POSS), carbon and ceramic nanotubes and fibers, nano-wires, and nano-fibers including single and multiwalled fullerenes, silica nano-gels, alumina nano-fibers, metal and metal oxide powders including alumina oxide, titanium oxide, gold, silver, platinum, and magnetic powders such as neodenium iron boron.

In some embodiments the material 18, or one or more components thereof, may be at characterized as being at least partially radio or MRI opaque.

Where material 18 is a thermoset, the material 18 may be deposited in multiple parts to enable a curing step. There may be additional processing steps including predeposition treatment of the surface 16 and post-deposition processing. Post-deposition processing may include a curing step that requires exposure of the material to an energy source such as IR or UV energy. As a result, depending on the particular substance selected to act as material 18 and the particular pattern employed the physical properties of the catheter 10 may be altered as desired.

Placement of the material 18 on the catheter surface 16 may be accomplished by a variety of deposition or coating methods. Such methods include but are not limited to the use of: solution coating, spray coating, thermal printing, piezo jet printing, contact printing, among others.

Figure 7:
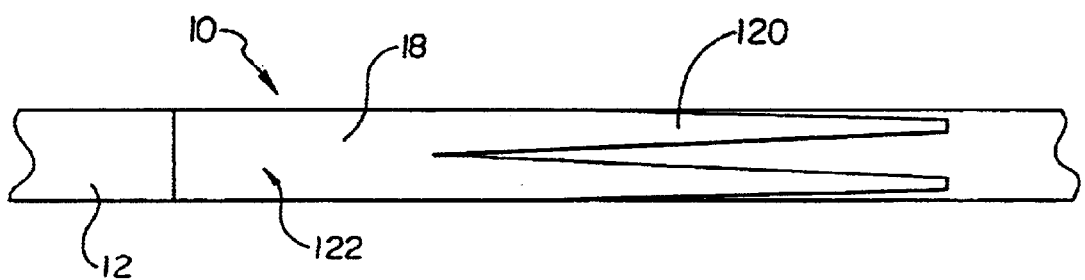
FIG. 7 is a side view of an embodiment of the invention showing a pattern of material placed on a section of catheter tubing.

As is illustrated in FIGS. 1–3, the material 18 may be placed on the catheter 10 in any pattern desired. Some additional patterns of material 18 deposition are shown in FIGS. 7–11. In FIG. 7 for example the material 18 comprises a plurality of stripes 120 which increase in thickness as the stripes 120 extend longitudinally along the length of the catheter 10. In some embodiments, the stripes 120 continue to increase until they contact one another to form a continuous band 122 about a portion of the catheter material 12.

Figure 8:
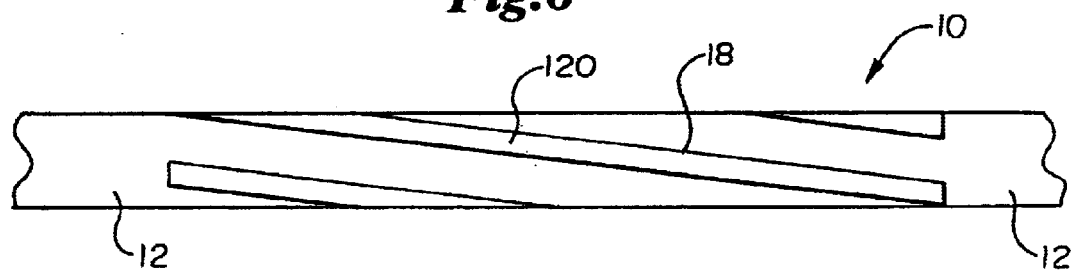
FIG. 8 is a side view of an embodiment of the invention showing a pattern of material placed on a section of catheter tubing.

In FIG. 8 the material 18 is applied as at least one helically oriented strip 120.

Figure 9:
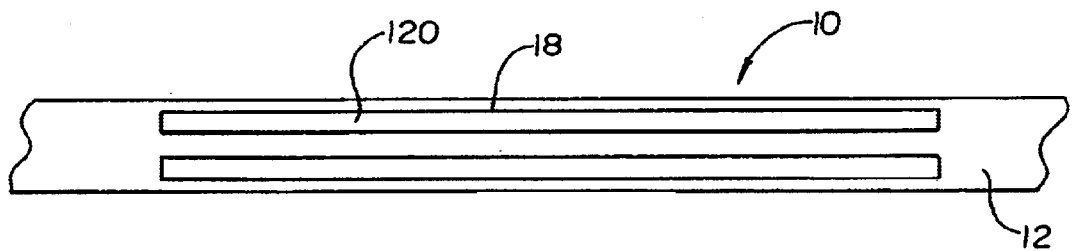
FIG. 9 is a side view of an embodiment of the invention showing a pattern of material placed on a section of catheter tubing.

In FIG. 9 the material 18 is deposited in a pattern of substantially parallel longitudinally oriented stripes 120.

Figure 10:
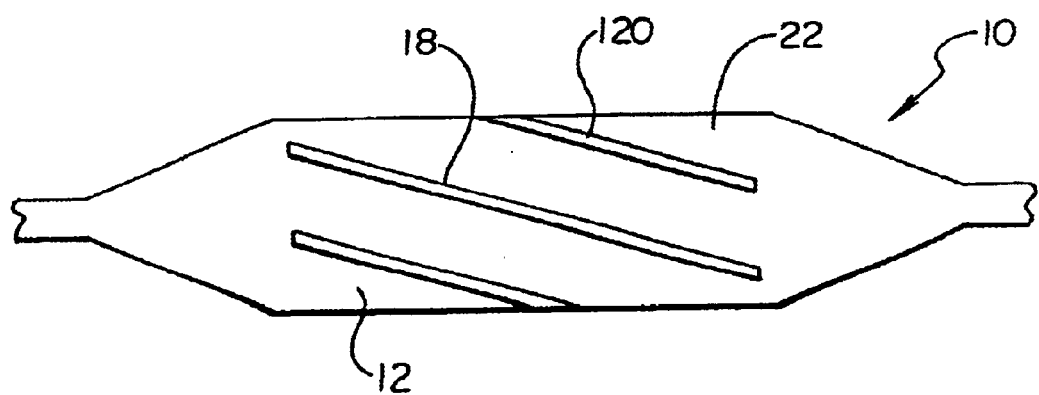
FIG. 10 is a side view of an embodiment of the invention showing a pattern of material placed on a section of catheter tubing.
Figure 11:
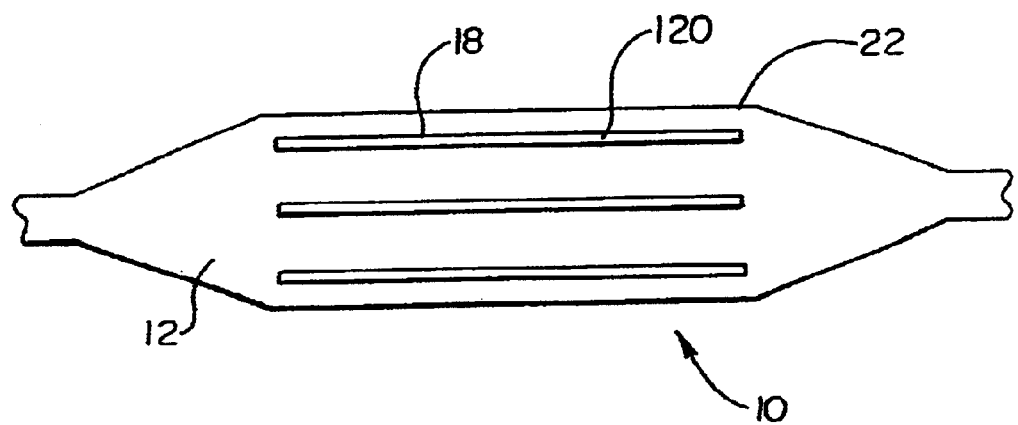
FIG. 11 is a side view of an embodiment of the invention showing a pattern of material placed on a section of catheter tubing.

In the embodiment shown in FIGS. 10 and 11, the material 18 is shown deposited only on the balloon portion 22 of a catheter 10. While the material 18 is shown limited only to the body portion of the balloon, in some embodiments, the material 18 may be selectively applied to the catheter 10 to be included on one or more cones and/or the body portion of the balloon 22.

The unique patterns of deposited material 18 used in the various embodiments described herein may provide a tubular member such as a catheter or balloon with stiffer or softer segments. In all of the various embodiments shown, the material 18 may be deposited on the external catheter surface 16 or the internal catheter surface as desired.

Figure 4:
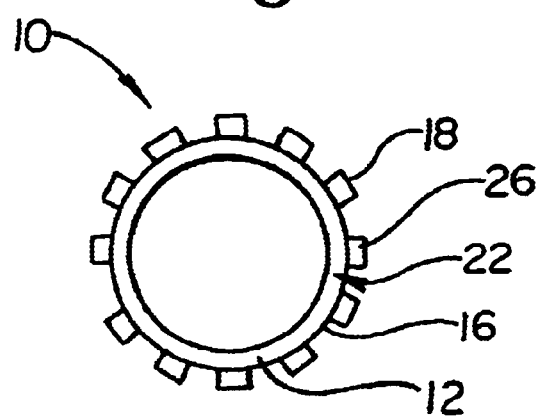
FIG. 4 is a cross-sectional view of an embodiment of the invention.

In the embodiments shown in FIGS. 1 and 2 the unique patterns of deposited material 18 may be raised to extend outward relative to the catheter surface 16. In FIG. 4, the profile of the catheter 10 may be seen wherein the material 18 extends outward from the surface 16 of the balloon 22.

Regardless of the particular pattern of material 18 applied to the surface 16, the pattern of material 18 can provide the catheter 10 with a textured surface capable of engaging a stent 20 or other medical device such as is shown in FIG. 3.

Stents typically comprise a framework 30 of interconnected struts and members 32 which define a plurality of openings 34 therebetween. Stents have a variety of strut patterns as well as a variety of opening sizes and shapes. Catheter 10 may be equipped with a pattern of deposited material 18 which acts to at least partially pass through the various openings of the stent in the reduced configuration. The unique pattern of material 18 may engage the stent 20 to retain the stent in the reduced predelivery state without the need for one or more retaining sheaths or members. Preferably, the individual protrusions 36 of the pattern of material 18 pass at least partially through correspondingly positioned openings 34 of the stent framework 30 to retain the stent 20 to the distal region 14 of the catheter 10 prior to delivery of the stent 20. The protrusions 36 engage the stent 20 by extending into the openings 34 to about 30 percent to about 100 percent of the thickness of the stent 20.

In addition to providing a catheter with improved medical device retaining characteristics, a tubular member that is provided with a coating or pattern of deposits of material may be provided with a variety of enhanced or modified characteristics. For example, by providing a pattern of material that is harder than the material of the tube, a catheter or other device made therefrom may be imparted with improved kink resistance due to the presence of the harder deposited material.

In at least one embodiment of the invention, the tube 12 is a balloon 22, such as is shown in FIG. 6. In such an embodiment the balloon 22 may be adapted to provide uniform inflation characteristics by application of one or more deposits of fibrous material 18.

Figure 5:
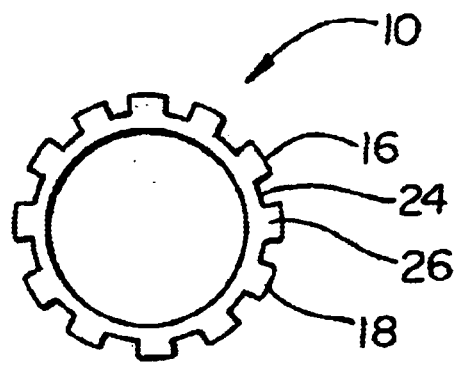
FIG. 5, labeled PRIOR ART, shows a side view of one type of known balloon during inflation.
Figure 6A:
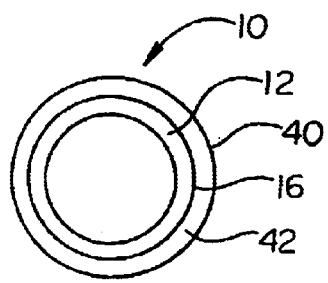
FIG. 6 is a side view of an embodiment of the invention directed to a balloon shown during inflation.
Figure 6B:
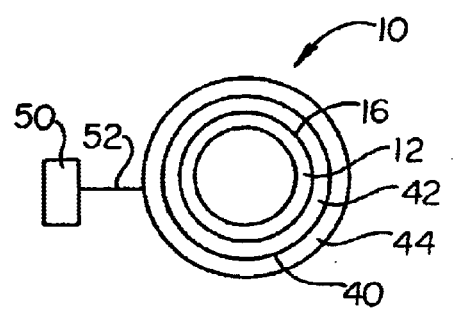
Figure 6C:
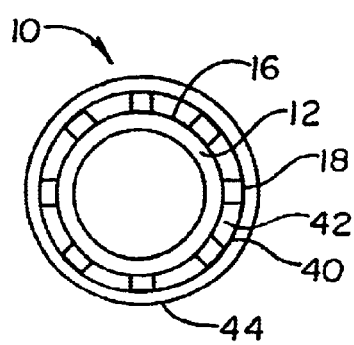
Figure 6D:
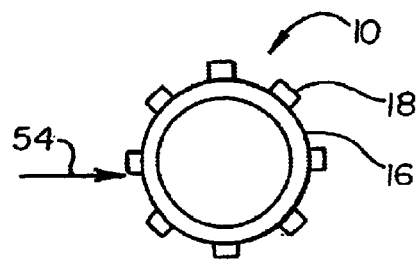
Figure 6E:
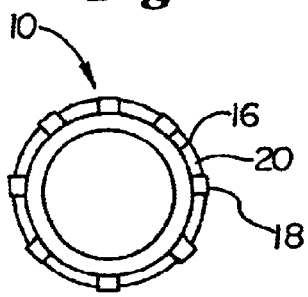
Figure 6F:
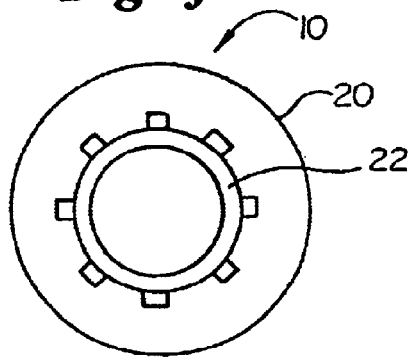

In FIG. 5, labeled PRIOR ART, an example of one type of previously known balloon is shown. As may be seen in FIG. 5 when this type of balloon is inflated such as for example, during a stent delivery procedure, the ends of the balloon tend to inflate first. This non-uniform inflation may provide for uneven delivery of the stent. In the embodiment of the invention shown in FIG. 6 however, struts or stripes 120 of material 18 are placed near the ends of the balloon 22. The stripes 120 act to transfer inflation stress from the ends of the balloon 22 to the middle portion of the balloon allowing the balloon to inflate more evenly. As a result, a balloon 22 may be utilized to provide more uniform deployment of a medical device such as stent 20. An alternative embodiment of a striped balloon is shown in FIGS. 10 and 11.

In addition to the embodiments described herein, in accordance with the above disclosure it is evident that catheters, balloons and other tubular members may be provided with deposits of material that will affect, enhance or otherwise modify one or more physical and/or performance characteristics of the tubular member. It should be recognized that in addition to those characteristics described herein, the present invention is also directed to any and all modifications of balloons and catheters utilizing the deposition of a pattern of fibrous material as described in accordance with the present invention herein.

In addition to being directed to the specific combinations of features claimed below, the invention is also directed to embodiments having other combinations of the dependent features claimed below and other combinations of the features described above.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

What is claimed is:

1. A substantially tubular member comprising:
   a body, the body constructed from a first material, the body having an external surface, at least a portion of the external surface having a predetermined pattern of a second material deposited thereon, the second material comprising a fibrous material, the predetermined pattern of the second material being deposited on the at least a portion of the external surface by at least one printing process selected from the group consisting of: solution coating, spray coating, thermal printing, piezo jet printing, contact printing and any combination thereof.

2. The substantially tubular member of claim 1 wherein the predetermined pattern of a second material defines at least one raised portion of the at least a portion of the external surface of the body.

3. The substantially tubular member of claim 1 wherein the predetermined pattern of a second material defines at least one substantially longitudinally oriented stripe on the at least a portion of the external surface of the body.

4. The substantially tubular member of claim 3 wherein the at least one substantially longitudinally oriented stripe comprises a plurality of stripes.

5. The substantially tubular member of claim 1 wherein the predetermined pattern of a second material is an irregular pattern.

6. The substantially tubular member of claim 1 wherein the predetermined pattern of a second material is a regular pattern.

7. The substantially tubular member of claim 1 wherein the body comprises a catheter.

8. The substantially tubular member of claim 7 wherein the external surface comprises a medical device receiving region, the predetermined pattern of a second material constructed and arranged to retain a medical device to the medical device receiving region prior to delivery of the medical device.

9. The substantially tubular member of claim 8 wherein the medical device receiving region is an expandable balloon.

10. The substantially tubular member of claim 9 wherein the medical device is a stent removably engaged to the at least a portion of the medical device receiving region, the predetermined pattern of a second material substantially engaging the stent prior to delivery.

11. The substantially tubular member of claim 1 wherein the predetermined pattern of a second material is a material that is softer than the first material.

12. The substantially tubular member of claim 1 wherein the predetermined pattern of a second material is a material that is harder than the first material.

13. The substantially tubular member of claim 1 wherein the predetermined pattern of a second material is selected from at least one member of the group consisting of: thermoplastics, thermosets, inorganic ceramic substances, metals and any combinations thereof.

14. The substantially tubular member of claim 1 wherein the fibrous material is a fibrous thermoset material, the fibrous thermoset material being selected from at least one member of the group consisting of organic thermoset compositions, inorganic thermoset compositions and any combination thereof.

15. The substantially tubular member of claim 1 wherein the fibrous material is substantially comprised of at least one organic fibrous material, the organic fibrous material being selected from at least one member of the group consisting of: linear resin systems containing epoxy, urethane, imide or urea functionalities; branched resin systems containing epoxy, urethane, imide, ester, ketene, sulphone or urea functionalities; vinyl or allylic functionalities, such as vinyl esters and cyanoacrylates; phenolic containing resins; silicone containing resins and any combinations thereof.

16. The substantially tubular member of claim 1 wherein the fibrous material is substantially comprised of at least one inorganic fibrous material, the at least one inorganic fibrous material comprising at least one thermoset composition having at least one member of the group consisting of alkoxides of silicon, aluminum, titanium, zirconcium and any combination thereof.

17. The substantially tubular member of claim 1 wherein the fibrous material comprises at least one thermoset composition, the at least one thermoset composition comprising liquid crystalline functionalities.

18. The substantially tubular member of claim 17 wherein the predetermined pattern of a second material comprises at least one resin composition having at least one planar aromatic functionality, the at least one planar aromatic functionality selected from at least one member of the group consisting of; 4-4'-di(2,3 epoxypropyloxy) phenyl benzoate, diamino diphenyl ester, 2,6 napthalene-di[4-(2-propenyloxy) benzoate], diamino diphenly sulfone, methylene dianiline, dicyatonapthalene, resorcinol diglycidyl ether, diaminonapthalene, napthalene diol, p-phenylene diamine and any combinations thereof.

19. The substantially tubular member of claim 14 wherein the fibrous thermoset material further comprises at least one filler, the at least on filler being selected from at least one member of the group consisting of: conventional fillers such as glass fiber and/or carbon; nanocomposite fillers such as intercalated and/or exfoliated clays such as, montmorillonite, hectorites, hydrotalcites, vermiculite, and/or laponite; monomeric silicates such as polyhedral oligomer silesequioxanes (POSS); carbon and ceramic nanotubes and fibers; nano-wires; nano-fibers including single and multiwalled fullerenes; silica nano-gels; alumina nano-fibers; metal and metal oxide powders including alumina oxide, titanium oxide, gold, silver, platinum; magnetic powders such as neodenium iron boron and any combinations thereof.

20. A method of producing a tubular member comprising the steps of:
   providing a tubular body made of a first material, the tubular body having an external surface; and
   depositing a predetermined pattern of a second material on at least a portion of the external surface of the tubular body by at least one printing process selected from the group consisting of: solution coating, spray coating, thermal printing, piezo jet printing, contact printing and any combination thereof, the second material comprising a fibrous material.

21. The method of claim 20 wherein the first material is a different material than the second material.

22. The method of claim 20 wherein the tubular body is a catheter.

23. The method of claim 20 wherein the tubular body is a balloon.

24. The method of claim 22 wherein the predetermined pattern of a second material on at least a portion of the external surface of the tubular body modifies at least one performance characteristic of the catheter.

25. The method of claim 24 wherein the predetermined pattern of a second material on at least a portion of the external surface of the tubular body modifies at least one performance characteristic of the balloon.

26. A substantially tubular member comprising:
   a body, the body constructed from a first material, the body having an external surface, at least a portion of the external surface having a predetermined pattern of a second material deposited thereon, the second material being harder than the first material, the predetermined pattern of the second material being deposited on the at least a portion of the external surface by at least one printing process selected from the group consisting of: solution coating, spray coating, thermal printing, piezo jet printing, contact printing and any combination thereof.

* * * * *